(12) United States Patent
Gazit et al.

(10) Patent No.: US 9,394,628 B2
(45) Date of Patent: Jul. 19, 2016

(54) METHOD OF FORMING A FIBER MADE OF PEPTIDE NANOSTRUCTURES

(71) Applicant: Ramot at Tel-Aviv University Ltd., Tel-Aviv (IL)

(72) Inventors: Ehud Gazit, Ramat-HaSharon (IL); Meital Reches, Beit-Hashmonai (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 4 days.

(21) Appl. No.: 14/061,771

(22) Filed: Oct. 24, 2013

(65) Prior Publication Data
US 2014/0044949 A1 Feb. 13, 2014

Related U.S. Application Data

(62) Division of application No. 11/659,150, filed as application No. PCT/IL2005/000589 on Jun. 5, 2005, now Pat. No. 8,568,637.

(60) Provisional application No. 60/592,523, filed on Aug. 2, 2004.

(51) Int. Cl.
| | | |
|---|---|---|
| A61K 38/00 | (2006.01) |
| C07K 16/00 | (2006.01) |
| D01F 4/00 | (2006.01) |
| C07K 5/065 | (2006.01) |
| C07K 5/06 | (2006.01) |
| C08J 5/18 | (2006.01) |
| D01D 5/00 | (2006.01) |
| D01F 1/10 | (2006.01) |
| D01F 6/68 | (2006.01) |

(52) U.S. Cl.
CPC .............. *D01F 4/00* (2013.01); *C07K 5/06078* (2013.01); *C07K 5/06191* (2013.01); *C08J 5/18* (2013.01); *D01D 5/00* (2013.01); *D01F 1/10* (2013.01); *D01F 6/68* (2013.01); *C08J 2300/16* (2013.01); *Y10T 428/253* (2015.01); *Y10T 428/298* (2015.01); *Y10T 442/60* (2015.04); *Y10T 442/614* (2015.04)

(58) Field of Classification Search
None
See application file for complete search history.

(56) References Cited

U.S. PATENT DOCUMENTS

| | | |
|---|---|---|
| 3,042,685 A | 7/1962 | Roussel |
| 2,920,080 A | 1/1965 | Bucourt et al. |
| 3,625,973 A | 12/1971 | Julia |
| 3,790,596 A | 2/1974 | Shkilkova et al. |
| 3,853,987 A | 12/1974 | Dreyer |
| 3,867,517 A | 2/1975 | Ling |
| 3,935,074 A | 1/1976 | Rubenstein et al. |
| 3,976,639 A | 8/1976 | Batcho et al. |
| 3,984,533 A | 10/1976 | Uzgiris |
| 4,036,945 A | 7/1977 | Haber |
| 4,299,917 A | 11/1981 | Berger et al. |
| 4,331,647 A | 5/1982 | Goldenberg |
| 4,626,540 A | 12/1986 | Capps et al. |
| 4,666,828 A | 5/1987 | Gusella |
| 4,801,531 A | 1/1989 | Frossard |
| 4,816,567 A | 3/1989 | Cabilly et al. |
| 4,873,316 A | 10/1989 | Meade et al. |
| 4,925,673 A | 5/1990 | Steiner et al. |
| 4,946,778 A | 8/1990 | Ladner et al. |
| 4,970,233 A | 11/1990 | McHugh |
| 5,013,556 A | 5/1991 | Woodle et al. |
| 5,116,824 A | 5/1992 | Miyata et al. |
| 5,171,505 A | 12/1992 | Lock |
| 5,270,163 A | 12/1993 | Gold et al. |
| 5,272,057 A | 12/1993 | Smulson et al. |
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,567,588 A | 10/1996 | Gold et al. |
| 5,569,825 A | 10/1996 | Lonberg et al. |
| 5,595,877 A | 1/1997 | Gold et al. |
| 5,625,126 A | 4/1997 | Lonberg et al. |
| 5,633,425 A | 5/1997 | Lonberg et al. |
| 5,637,459 A | 6/1997 | Burke et al. |
| 5,643,768 A | 7/1997 | Kawasaki |
| 5,658,754 A | 8/1997 | Kawasaki |
| 5,659,041 A | 8/1997 | Pollak et al. |
| 5,661,016 A | 8/1997 | Lonberg et al. |
| 5,683,867 A | 11/1997 | Biesecker et al. |
| 5,705,337 A | 1/1998 | Gold et al. |
| 5,831,002 A | 11/1998 | Haupt et al. |
| 5,856,928 A | 1/1999 | Yan |

(Continued)

FOREIGN PATENT DOCUMENTS

| | | |
|---|---|---|
| DE | 3412445 | 10/1985 |
| DE | 10043282 | 3/2002 |

(Continued)

OTHER PUBLICATIONS

Gorbitz et al. Nanotube Formation by Hydrophobic Dipeptides, Chem. Eur J., 2001, 7 No. 23.*

(Continued)

*Primary Examiner* — Jeanette Lieb

(57) ABSTRACT

A method of forming a fiber made of peptide nanostructures is disclosed. The method comprises: providing peptide nanostructures in solution, and fiberizing the solution thereby forming at least one fiber of the peptide nanostructures. Also disclosed are methods of forming films and other articles using the peptide nanostructures.

11 Claims, 10 Drawing Sheets

(56) References Cited

U.S. PATENT DOCUMENTS

| | | | |
|---|---|---|---|
| 5,916,642 A | 6/1999 | Chang | |
| 5,977,302 A | 11/1999 | Palmer et al. | |
| 6,110,590 A | 8/2000 | Zarkoob et al. | |
| 6,162,828 A | 12/2000 | Fukuda et al. | |
| 6,235,876 B1 | 5/2001 | Palmer et al. | |
| 6,251,625 B1 | 6/2001 | Bommarius et al. | |
| 6,255,286 B1 | 7/2001 | Yanai et al. | |
| 6,300,141 B1 | 10/2001 | Segal et al. | |
| 6,303,567 B1 | 10/2001 | Findeis et al. | |
| 6,309,669 B1 | 10/2001 | Setterstrom et al. | |
| 6,326,174 B1 | 12/2001 | Joyce et al. | |
| 6,359,112 B2 | 3/2002 | Kapurniotu et al. | |
| 6,361,861 B2 | 3/2002 | Gao et al. | |
| 6,376,233 B1 | 4/2002 | Wolf et al. | |
| 6,472,436 B1 | 10/2002 | Schubert et al. | |
| 6,593,339 B1 | 7/2003 | Eek et al. | |
| 6,610,478 B1 | 8/2003 | Takle et al. | |
| 6,613,875 B1 | 9/2003 | Ghadiri | |
| 6,617,114 B1 | 9/2003 | Fowlkes et al. | |
| 6,677,153 B2 | 1/2004 | Iversen | |
| 6,762,331 B2 | 7/2004 | Hong et al. | |
| 6,858,318 B2 | 2/2005 | Kogiso et al. | |
| 6,976,639 B2 | 12/2005 | Williams et al. | |
| 7,045,537 B1 | 5/2006 | Woolfson et al. | |
| 7,491,699 B2 * | 2/2009 | Reches et al. | 514/1.1 |
| 7,504,383 B2 | 3/2009 | Gazit et al. | |
| 7,786,086 B2 | 8/2010 | Reches et al. | |
| 8,017,586 B2 | 9/2011 | Gazit et al. | |
| 8,053,554 B2 * | 11/2011 | Reches et al. | 530/300 |
| 8,350,004 B2 | 1/2013 | Reches et al. | |
| 8,420,605 B2 | 4/2013 | Ulijn et al. | |
| 8,501,697 B2 | 8/2013 | Gazit et al. | |
| 8,568,637 B2 | 10/2013 | Gazit et al. | |
| 8,796,023 B2 | 8/2014 | Reches et al. | |
| 2001/0041732 A1 | 11/2001 | Gurley et al. | |
| 2002/0006954 A1 | 1/2002 | Hensley et al. | |
| 2002/0086067 A1 | 7/2002 | Choi et al. | |
| 2002/0151506 A1 | 10/2002 | Castillo et al. | |
| 2002/0155992 A1 | 10/2002 | Xu | |
| 2003/0144185 A1 | 7/2003 | McGimpsey | |
| 2003/0158237 A1 | 8/2003 | Saragovi et al. | |
| 2003/0211007 A1 | 11/2003 | Maus et al. | |
| 2003/0225155 A1 | 12/2003 | Fernandez-Pol et al. | |
| 2004/0001893 A1 | 1/2004 | Stupp et al. | |
| 2004/0029830 A1 | 2/2004 | Hebert | |
| 2004/0052928 A1 | 3/2004 | Gazit | |
| 2004/0152672 A1 | 8/2004 | Carson et al. | |
| 2004/0258726 A1 | 12/2004 | Stupp et al. | |
| 2005/0069950 A1 | 3/2005 | Haynie | |
| 2005/0124535 A1 | 6/2005 | McGimpsey | |
| 2006/0079454 A1 | 4/2006 | Reches et al. | |
| 2006/0079455 A1 | 4/2006 | Gazit et al. | |
| 2006/0089380 A1 | 4/2006 | Barnham et al. | |
| 2006/0089489 A1 | 4/2006 | Onizuka et al. | |
| 2006/0194777 A1 | 8/2006 | Gazit et al. | |
| 2006/0234947 A1 | 10/2006 | Gazit | |
| 2007/0015813 A1 | 1/2007 | Carter et al. | |
| 2007/0021345 A1 | 1/2007 | Gazit | |
| 2007/0099840 A1 | 5/2007 | Ulijn et al. | |
| 2007/0135334 A1 | 6/2007 | Gazit | |
| 2007/0138007 A1 | 6/2007 | Yemini et al. | |
| 2007/0298043 A1 | 12/2007 | Gazit et al. | |
| 2008/0009434 A1 | 1/2008 | Reches et al. | |
| 2009/0061190 A1 | 3/2009 | Gazit et al. | |
| 2009/0121709 A1 | 5/2009 | Gazit et al. | |
| 2009/0123553 A1 | 5/2009 | Reches et al. | |
| 2009/0175785 A1 | 7/2009 | Gazit et al. | |
| 2009/0263429 A1 | 10/2009 | Ulijn et al. | |
| 2010/0291828 A1 | 11/2010 | Reches et al. | |
| 2011/0266517 A1 | 11/2011 | Gazit et al. | |
| 2012/0063276 A1 | 3/2012 | Reches et al. | |
| 2013/0075703 A1 | 3/2013 | Gazit et al. | |
| 2014/0027655 A1 | 1/2014 | Reches et al. | |

FOREIGN PATENT DOCUMENTS

| | | |
|---|---|---|
| EP | 0081122 | 6/1983 |
| EP | 0421946 | 4/1991 |
| EP | 0966975 | 9/2005 |
| EP | 1583713 | 10/2005 |
| FR | 1373316 | 9/1964 |
| JP | 59-044313 | 3/1984 |
| JP | 60-040061 | 3/1985 |
| JP | 63-044895 | 2/1988 |
| JP | 02-295923 | 12/1990 |
| JP | 10-245342 | 9/1998 |
| JP | 2000-193661 | 7/2000 |
| JP | 2007-506732 | 3/2007 |
| WO | WO 80/00789 | 1/1980 |
| WO | WO 97/16191 | 5/1997 |
| WO | WO 98/20135 | 5/1998 |
| WO | WO 99/42102 | 8/1999 |
| WO | WO 99/58652 | 11/1999 |
| WO | WO 00/24390 | 5/2000 |
| WO | WO 01/05421 | 1/2001 |
| WO | WO 01/10457 | 2/2001 |
| WO | WO 01/45726 | 6/2001 |
| WO | WO 01/49281 | 7/2001 |
| WO | WO 01/49307 | 7/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/063760 | 8/2003 |
| WO | WO 03/069033 | 8/2003 |
| WO | WO 03/070269 | 8/2003 |
| WO | WO 03/077866 | 9/2003 |
| WO | WO 2004/050693 | 6/2004 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 4/2005 |
| WO | WO 2005/085867 | 9/2005 |
| WO | WO 2006/006172 | 1/2006 |
| WO | WO 2006/013552 | 2/2006 |
| WO | WO 2006/018850 | 2/2006 |
| WO | WO 2006/020681 | 2/2006 |
| WO | WO 2006/027780 | 3/2006 |
| WO | WO 2007/029003 | 3/2007 |
| WO | WO 2007/043048 | 4/2007 |

OTHER PUBLICATIONS

Official Action Dated Jan. 13, 2014 From the US Patent and Trademark Office Re. U.S. Appl. No. 12/083,222.
Official Action Dated Feb. 19, 2014 From the US Patent and Trademark Office Re. U.S. Appl. No. 13/671,667.
Official Action Dated May 30, 2014 From the US Patent and Trademark Office Re. U.S. Appl. No. 13/671,667.
Notification of Non-Compliant Appeal Brief (37 CFR 41.37) Dated Jun. 19, 2014 From the US Patent and Trademark Office Re. U.S. Appl. No. 12/083,222.
Communication Pursuant to Article 94(3) EPC Dated Dec. 16, 2013 From the European Patent Office Re. Application No. 05747261.5.
Official Action Dated Dec. 11, 2014 From the US Patent and Trademark Office Re. U.S. Appl. No. 12/083,222.
Yahoo "Convert mmol/L to mg/ml?", Standard Conversion Site, Yahoo Answers, 1 P., 2013.
Applicant-Initiated Interview Summary Dated Oct. 11, 2013 From the US Patent and Trademark Office Re. U.S. Appl. No. 12/843,097.
Ex Parte Quayle Official Action Dated May 17, 2013 From the US Patent and Trademark Office Re. U.S. Appl. No. 11/659,150.
Notice of Allowability Dated May 21, 2010 From the US Patent and Trademark Office Re.: U.S. Appl. No. 11/662,136.
Notice of Allowance Dated Apr. 1, 2013 From the US Patent and Trademark Office Re. U.S. Appl. No. 13/680,217.
Notice of Allowance Dated Mar. 7, 2011 From the US Patent and Trademark Office Re.: U.S. Appl. No. 12/318,653.

(56) References Cited

OTHER PUBLICATIONS

Notice of Allowance Dated Jun. 9, 2011 From the US Patent and Trademark Office Re.: U.S. Appl. No. 12/318,619.
Notice of Allowance Dated Jul. 12, 2012 From the US Patent and Trademark Office Re.: U.S. Appl. No. 13/179,638.
Notice of Allowance Dated Sep. 17, 2008 From the US Patent and Trademark Office Re.: U.S. Appl. No. 11/148,266.
Notice of Allowance Dated Jun. 18, 2008 From the US Patent and Trademark Office Re.: U.S. Appl. No. 11/148,262.
Notice of Allowance Dated Sep. 23, 2010 From the US Patent and Trademark Office Re.: U.S. Appl. No. 11/591,613.
Notice of Allowance Dated Jun. 26, 2013 From the US Patent and Trademark Office Re. U.S. Appl. No. 11/659,150.
Notice of Allowance Dated Mar. 26, 2010 From the US Patent and Trademark Office Re.: U.S. Appl. No. 11/662,136.
Notice of Allowance Dated Aug. 31, 2012 From the US Patent and Trademark Office Re. U.S. Appl. No. 13/290,147.
Official Action Dated Apr. 1, 2010 From the US Patent and Trademark Office Re.: U.S. Appl. No. 11/591,613.
Official Action Dated Apr. 3, 2009 From the US Patent and Trademark Office Re.: U.S. Appl. No. 11/662,136.
Official Action Dated Feb. 8, 2013 From the US Patent and Trademark Office Re. U.S. Appl. No. 11/659,150.
Official Action Dated Jun. 9, 2010 From the US Patent and Trademark Office Re.: U.S. Appl. No. 11/662,136.
Official Action Dated Dec. 10, 2010 From the US Patent and Trademark Office Re.: U.S. Appl. No. 12/318,619.
Official Action Dated Dec. 11, 2009 From the US Patent and Trademark Office Re.: U.S. Appl. No. 12/318,653.
Official Action Dated Jun. 11, 2012 From the US Patent and Trademark Office Re. U.S. Appl. No. 11/659,150.
Official Action Dated Jan. 12, 2012 From the US Patent and Trademark Office Re. U.S. Appl. No. 13/179,638.
Official Action Dated Jul. 14, 2008 From the US Patent and Trademark Office Re.: U.S. Appl. No. 11/662,136.
Official Action Dated Feb. 15, 2008 From the US Patent and Trademark Office Re.: U.S. Appl. No. 11/148,262.
Official Action Dated Jul. 15, 2011 From the US Patent and Trademark Office Re. U.S. Appl. No. 12/083,222.
Official Action Dated Mar. 16, 2011 From the US Patent and Trademark Office Re. U.S. Appl. No. 12/083,222.
Official Action Dated Apr. 17, 2012 From the US Patent and Trademark Office Re. U.S. Appl. No. 12/083,222.
Official Action Dated Aug. 19, 2013 From the US Patent and Trademark Office Re. U.S. Appl. No. 12/843,097.
Official Action Dated Sep. 19, 2007 From the US Patent and Trademark Office Re.: U.S. Appl. No. 11/148,262.
Official Action Dated Jul. 22, 2010 From the US Patent and Trademark Office Re.: U.S. Appl. No. 12/318,653.
Official Action Dated Jun. 22, 2009 From the US Patent and Trademark Office Re.: U.S. Appl. No. 12/318,653.
Official Action Dated Nov. 26, 2008 From the US Patent and Trademark Office Re.: U.S. Appl. No. 11/662,136.
Official Action Dated Sep. 27, 2007 From the US Patent and Trademark Office Re.: U.S. Appl. No. 11/148,266.
Official Action Dated Jan. 29, 2013 From the US Patent and Trademark Office Re. U.S. Appl. No. 12/843,097.
Official Action Dated Mar. 29, 2013 From the US Patent and Trademark Office Re. U.S. Appl. No. 12/083,222.
Official Action Dated Apr. 30, 2007 From the US Patent and Trademark Office Re.: U.S. Appl. No. 11/148,262.
Official Action Dated Aug. 30, 2010 From the US Patent and Trademark Office Re.: U.S. Appl. No. 12/318,619.
Official Action Dated Jun. 30, 2010 From the US Patent and Trademark Office Re.: U.S. Appl. No. 11/662,136.
Second Notice of Allowance Dated Sep. 16, 2008 From the US Patent and Trademark Office Re.: U.S. Appl. No. 11/148,262.
Ajayan et al. "Application of Carbon Nanotubes", Topics of Applied Physics, 80: 391-425, 2001.

Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1): 68-76, 2000.
Altland et al. "Potential Treatment of Transthyretin-Type Amyloidoses by Sulfite", Neurogenetics, 2: 183-188, 1999.
Appukkuttan et al. "Microwave Enhanced Formation of Electron Rich Arylboronates", Synlett, 8: 1204-1206, 2003. Figs., Scheme 4, Compounds 5A, 5B, 5C, 5D.
Azriel et al. "Analysis of the Minimal Amyloid-Forming Fragment of the Islet Amyloid Polypeptide", The Journal of Biological Chemistry, 276(36): 34156-34161, 2001.
Balaram "De Novo Design: Backbone Conformational Constraints in Nucleating Helices and ?-Hairpins", Journal of Peptide Research, 54: 195-199, 1999.
Barrett et al. "Multiple Mechanisms for the Carcinogenic Effects of Asbestos and Other Mineral Fibers", Environmental Helath Perspectives, 81: 81-89, 1989.
Berson et al. "Proprotein Convertase Cleavage Liberates a Fibrillogenic Fragment of a Resident Glycoprotein to Initiate Melanosome Biogenesis", Journal of Cell Biology, 161(3): 521-533, 2003.
Beugelmans Database Crossfire Beilstein [Online], Beilstein Institut zur F?rderung der Chemischen Wissenschaften, Frankfurt am Main, DE, Database Accession No. 116671 (BRN) Compounds INDOL-2-YL-Methanol & Beugelmans R.: Bulletin de la Soci?t? Chimique Fran?aise, p. 335-336, 1969.
Bong et al. "Self-Assembling Organic Nanotubes", Angewandte Chemie, International Edition,40:988-1011, 2001.
Changqing et al. "Amyloid-Like Formation by Self-Assembly of Peptidolipids in Two Dimensions", Langmuir, 20: 8641-8645, 2004.
Chapman et al. "Role of *Escherichia coli* Curli Operons in Directing Amyloid Fiber Emulation", Science, 295(5556): 851-855, 2002. Abstract.
Cherny et al. "The Formation of *Escherichia coli* Curli Amyloid Fibrils is Mediated by Prion-Like Peptide Repeals", Journal of Molecular Biology, 352(2): 245-252, 2005.
Cherny et al. "The YefM Antitoxin Defines a Family of Natively Unfolded Proteins", The Journal of Biological Chemistry, 279(9): 8252-8261, Feb. 27, 2004.
Chou et al. "Empirical Predictions of Protein Conformation", Annual Reviews in Biochemistry, 47: 251-276, 1978.
Claessen et al. "A Novel Class of Secreted Hydrophodic Proteins is Involved in Aerial Hyphae Formation in Streptomyces Coelicolor by Forming Amyloid-Like Fibrils", Genes & Development, 17: 1714-1726, 2003.
Clark et al. "Self-Assembling Cyclic ?3-Peptide Nanotubes as Artificial Transmembrane Ion Channels", Journal of the American Chemical Society, 120: 651-656, 1998.
Cohen et al "Inhibition of Amyloid Fibril Formation and Cytotoxicity by Hydroxyindole Derivatives", Biochemistry, 45: 4727-4735, 2006. p. 4728, col. 1, Last §, p. 4728, col. 2, § 2, p. 4729, col. 1, Last §, col. 2, § 2, Fig.1, 4, p. 4732, col. 2, § 2, 3, p. 4733, co1. 2, § 4.
Elliot et al. "The Chaplins: A Family of Hydrophobic Cell-Surface Proteins Involved in Aerial Mycelium Formation in Streptomyces Coelicolor", Genes & Development, 17: 1727-1740, 2003.
Engelberg-Kulka et al. "Bacterial Programmed Cell Death Systems as Targets for Antibiotics", Trends in Microbiology, XP002477942, 12(2): 66-71, Feb. 2004.
Forloni et al. "Anti-Amyloidogenic Activity of Tetracyclines: Studies In Vitro", FEBS Letters, 487(3): 404-407, 2001. Abstract, Results, Figs.1, 3.
Ganesh et al. "Circular Dichroism and Fourier Transform Infrared Spectroscopic Studies on Self-Assembly of Tetrapeptide Derivative in Solution and Solvated Film", The Journal of Peptide Research: Official Journal of the American Peptide Society, XP002529296, 61(3): 122-128, Mar. 2003.
Gazit "A Possible Role for 'Phi'-Stacking in the Self-Assembly of Amyloid Fibrils", The FASEB Journal, 16: 77-83, 2002.
Gazit "Diversity for Self-Assembly", Nature Chemistry, 2: 1010-1011, Dec. 2010.
Gazit "Mechanisms of Amyloid Fibril Self-Assembly and Inhibition Model Short Peptides as a Key Research Tool", The FEBS Journal, 272: 5971-5978, 2005.

(56) References Cited

OTHER PUBLICATIONS

Gazit "Mechanics Studies of Process of Amyloid Fibrils Formation by the Use of Peptide Fragments and Analogues: Implications for the Design of Fibrillization Inhibitors", Current Medicinal Chemistry, 9: 1725-1735, 2002.
Ghadiri et al. "Artificial Transmembrane Ion Channels From Self-Assembling Peptide Nanotubes", Nature, 369(6478): 301-304, 1994.
Ghadiri et al. "Self-Assembling Organic Nanotubes Based on a Cyclic Peptide Architecture", Nature, XP002936460, 366: 324-327, Dec. 25, 1993.
Goerbitz "Nanotube Formation by Hydrophobic Dipeptides", Chemical European Journal, Chemistry, XP001180634, 7(23): 5153-5159, Dec. 3, 2001.
Gorman et al. "Alzheimer Beta-Amyloid Peptides, Structures of Amyloid Fibrils and Alternate Aggregation Products", Biopolymers, 60: 381-394, 2001.
Grady et al. "Axe-Txe, A Broad-Spectrum Proteic Toxin—Antitoxin System Specified by a Multidrug-Resistant, Clinical Isolate of *Enterococcus faecium*", Molecular Microbiology, 47(5): 1419-1432, 2003. Abstract, p. 1424, col. 1—p. 1426, col. 2, Fig.5.
Grateau "Le Curli du Coli: Une Vari?t? Physiologique d'Amylose [Coli's Curli or How Amyloid Can be Physiological.]", M?dccinc Sciences, 18(6-7): 664, Jun.-Jul. 2002.
Haldar et al. "First Crystallographic Signature of the Highly Ordered Supramolecular Helical Assemblage From a Tripeptide Containing a Non-Coded Amino Acid", Tetrahedron Letters, XP004343975, 43(14): 2653-2656, 2002. Abstract.
Hartgerink et al. "Peptide Nanotubes and Beyond", Chemistry, XP002276851, 4(8): 1367-1372, 1998.
Hartgerink et al. "Self-Assembling Peptide Nanotubes", Journal of the American Chemical Society, 118: 43-50, 1996.
Hayden el al. "'A' is for Amylin and Amyloid in Type 2 Diabetes Mellitus", JOP Journal of the Pancreas (Online), 2(4): 124-139, 2001.
Hiemenz "Aggregation", Principles of Colloid and Surface Chemistry, 2nd Ed., Chap.1.7: 27-32, 1986.
Higaki et al. "Regulation of Drug Absorption From Small Intestine by Enteric Nervous System I: A Poorly Absorbable Drug Via Passive Diffusion", Drug Metabolism and Pharmacokinctics, 19(3): 198-205, 2004.
Hirst et al. "Biocatalytic Induction of Supramolecular Order", Nature Chemistry, 2: 1089-1094, Dec. 2010.
Holmes et al. "Extensive Neurite Outgrowth and Active Synapse Formation on Self-Assembling Peptide Scaffolds", Proc. Natl. Acad. Sci. USA, XP002213924, 97(12): 6728-6733, Jun. 6, 2000.
Honma et al. "Use of a Thromboxane A2 Antagonist or Synthase Inhibitor for Treating Central Nervous System Diseases, e.g. Alzheimer Type Dementia," Database WPI, Section Ch. Week 200039, Derwent Publications, Class B05, AN 2000-451668, Jun. 2, 2000. Abstract. & WO 00/30683.
Horne et al. "A Heterocyclic Peptide Nanotube", Journal of the American Chemical Society, JACS, XP002276671, 125(31): 9372-9376, Aug. 6, 2003. Abstract.
Hoyle et al. "Pseudomonas Aeruginosa Biofilm as a Diffusion Barrier to Piperacillin", Antimicrobial Agents and Chemotherapy, 36(9): 2054-2056, 1992.
Huang et al. "A Review on Polymer Nanofibers by Electrospinning and Their Applications in Nanocomposites", Composites Science and Technology, 63: 2223-2253, 2003.
Inglot "Comparison of the Antiviral Activity In Vitro of Some Non-Steroidal Anti-Inflammatory Drugs", Journal of General Virology, 4(2): 203-214, 1969.
Jack et al. "The Organization of Aromatic Side Groups in an Amyloid Fibril Probed by Solid-State 2H and 19F NMR Spectroscopy", Journal of the American Chemical Society, JACS, 128: 8098-8099, 2006.
Jayawarna et al. "Nanostructured Hydrogels for Three-Dimensional Cell Culture Through Self-Assembly of Fluorenylmethoxycarbonyl-Dipeptides", Advanced Materials, XP002446151, 18: 611-614, 2006.
Jin "Electrospinning Bombyx Mon Silk With Poly (Ethylene Oxide)" Biomacromolecules, 3: 1233-1239, 2002.

Kaplan "Fibrous Proteins-Silk as a Model System", Polymer Degradation and Stability, 59: 25-32, 1998.
Kerman et al. "Peptide Nucleic Acid-Modified Carbon Nanotube Field-Effect Transistor for Ultra-Sensitive Real-Time Detection of DNA Hybridization", NanoBiotechnology, 1(1): 65-70, Mar. 2005.
Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, Class B02, AN 2003-286683, Jan. 20, 2003. Abstract. & RU 2196568.
Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.
Kocisko et al. "New Inhibitors of Scrabie-Associated Prion Protein Formation in a Library of 2,000 Drugs and Natural Products", Journal of Virology, 77(19): 10288-10294, 2003.
Kon-Ya et al. "Indole Derivatives as Potent Inhibitors of Larval Settlement by the Barnacle, Balanus Amphitrite", Bioscience, Biotechnology and Biochemistry, 58(12): 2178-2181, 1994. Compound 102.
Kubik "High-Performance Fibers From Spider Silk", Angewandte Chemie, International Edition, 41(15): 2721-2723, 2002.
Lansbury Jr. "Following Nature's Anti-Amyloid Strategy", Nature Biotechnology, 19(2): 112-113, 2001.
Lashuel et al. "New Class of Inhibitors of Amyloid-? Fibril Formation. Implications for the Mechanism of Pathogenesis in Alzheimer's Disease", The Journal of Biological Chemistry, 277(45): 42881-42890, 2002.
Lazaris et al. "Spider Silk Fibers Spun From Soluble Recombinant Silk Produced in Mammalian Cells", Science, 295: 472-476, 2002. p. 474-475.
Lee et al. "Anti-Diabetic Constituent From the Node of Lotus Rhizome (Nelumbo Nucifera Gaertn)", Natural Product Sciences, 7(4), 107-109, 2001.
Lee et al. "Virus-Based Fabrication of Micro- and Nanofibers Using Electrospinnig", Nano Letters, 4(3): 387-390, Mar. 2004.
Li et al. "Amyloid-Like Formation by Self-Assembly of Peptidolipids in Two Dimensions", Langmuir: The ACS Journal of Surfaces and Colloids, XP002529300, 20(20): 8641-8645, Aug. 24-Sep. 28, 2004.
Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.
Losert et al. "Effect of Indole 3 Alkanecarboxylic Acifs on Glucose Utilization in Rats", Arzneimittel-Forschung/Drug Research, 25(6): 880-887, 1975.
Ludtke et al. "Membrane Pores Induced by Magainin", Biochemistry, 35: 13712-13728, 1996.
Lutolf et al. "Cell-Responsive Synthetic Hydrogels", Advanced Materials, 15(11): 888-892, Jun. 5, 2003.
MacPhee et al. "Engineered and Designed Peptide-Based Fibrous Biomaterials", Current Opinion in Solid State and Materials Science, XP002529298, 8(2): 141-149, Mar. 2004.
Mah et al. "A Genetic Basis for Pseudomonas Aeruginosa Biofilm Antibiotic Resistance", Nature, 426: 306-310, 2003.
Mahler et al. "Rigid, Self-Assembled Hydrogel Composed of a Modified Aromatic Dipeptide", Advanced Materials, XP002446150, 18(11): 1365-1370, 2006.
Maji et al. "Fibril-Forming Model Synthetic Peptides Containing 3-Aminophenylacetic Acid", Tetrahedron, XP004390176, 58(43): 8695-8702, 2002.
Martin et al. "The Emerging Field of Nanotube Biotechnology", Nature Reviews: Drug Discovery, 2(1): 29-37, Jan. 2003. Abstract.
Matsui et al. "Crystalline Glyclylglycine Bolaamphiphile Tubules and Their pH-Sensitive Structural Transformation" The Journal of Physical Chemistry B, 104(15): 3384-3386, 2000.

(56) References Cited

OTHER PUBLICATIONS

Meluleni et al. "Mucoid Pseudomonas Aeruginosa Growing in a Biofilm in Vitro Are Killed by Opsonic Antibodies to the Mucoid Exopolysaccharide Capsule But Not by Antibodies Produced During Chronic Lung Infection in Cystic Fibrosis Patients,", Journal of Immunology, 155: 2029-2038, 1995.

Murphy et al. "Biofilm Formation by Nontypeable Haemophilus Influenzae: Strain Variability, Outer Membrane Antigen Expression and Role of Pili", BMC Microbiology, 2(7): 1471-2180, 2002.

Murphy et al. "Matrix Metalloproteinase Degradation of Elastin, Type IV Collagen and Proteoglycan", Biochemistry Journal, 277: 277-279, 1991.

Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.

NCBI "Collagen Type IV A6 Chain [*Homo Sapiens*]", GenBank NCBI, GenBank Accession No. AAB19038, Nov. 18, 1996.

Nishimura et al. "PAR-1 Kinase Plays an Initiator Role in a Temporally Ordered Phosphorylation Process That Confers Tau Toxicity in Drosophila", Cell, 116: 671-682, Mar. 5, 2004.

Oza et al. "Synthesis and Evaluation of Anthranilic Acid-Based Transthyretin Amyloid Fibril Inhibitors", Bioorganic & Medicinal Chemistry Letters 9(1): 1-6, 1999.

Pavia et al. "Antimicrobial Activity of Nicotine Against a Spectrum of Bacterial and Fungal Pathogens", Journal of Medical Microbiology, 49(7): 675-676, 2000.

Perutz et al. "Amyloid Fibers Are Water-Filled Nanotubes", Proc. Natl. Acad. Sci. USA, PNAS, 99(8): 5591-5595, Apr. 16, 2002.

Peterson et al. "Inhibiting Transthyretin Conformational Chamges That Lead to Amyloid Fibril Formation", Proc. Natl. Acad. Sci. USA, 95: 12956-12960, 1998.

Pispisa et al. "A Spectroscopic and Molecular Mechanics Investigation on a Series of AIB-Based Linear Peptides and a Peptide Template, Both Containing Tryptophan and a Nitroxide Derivative as Probes", Biopolymers, 53: 169-181, 2000.

Rajagopal et al. "Self-Assembling Peptides and Proteins for Nanotechnological Applications", Current Opinion in Structural Biology, XP002529297, 14(4): 480-486, Aug. 2004.

Reches et al. "Amyloid Fibril Formation by Pentapeptide and Tetrapeptide Fragments of Human Calcitonin", The Journal of Biological Chemistry, XP002276670, 277(38): 35475-35480, 2002.

Reches et al. "Casting Metal Nanowires Within Discrete Self-Assembled Peptide Nanotubes", Science, XP002276672, 300(5619): 625-627, Apr. 25, 2003. "Supporting Online Materials", Science [Online], 300(5619): 1-9, Apr. 25, 2003.

Reches et al. "Designed Aromatic Homo-Dipeptides: Formation of Ordered Nanostructures and Potential Nanotechnological Applications", Physical Biology, 3: S10-S19, 2006.

Reches et al. "Formation of Closed-Cage Nanostructures by Self-Assembly of Aromatic Dipeptides", Nano Letters, 4(4): 581-585, 2004.

Reches et al. "Self-Assembly of Peptide Nanotubes and Amyloid-Like Structures by Charged-Termini-Capped Diphenylalanine Peptide Analogues", Israel Journal of Chemistry, XP009087914, 45(3): 363-371, Jun. 30, 2005.

Reches et al. "Supporting Online Material", Science, 300(5619): 1-9, Apr. 25, 2003.

Robinson et al. "The Design of a Biochip: A Self-Assembling Molecular-Scale Memory", Protein Engineering, 1(4): 295-300, 1987.

Ryadnov et al. "Engineering the Morphology of a Self-Assembling Protein Fibre", Nature Materials, XP002529299, 2(5): 329-332, May 2003.

Sacchettini et al. "Therapeutic Strategies for Human Amyloid Diseases", Nature Reviews: Drug Discovery, 1: 267-275, 2002.

Soppimath et al. "Biodegradable Polymeric Nanoparticles as Drug Delivery Devices", Journal of Controlled Release, 70: 1-20, 2001.

Soto ct al. "Beta-Sheet Breaker Pcptidcs Inhibit Fibrillogenesis in a Rat Brain Model of Amyloidosis: Implications for Alzheimer's Therapy", Nature Medicine 4(7): 822-826, 1998.

Stephenson et al. "The 'Promiscuous Drug Concept' With Applications to Alzheimer's Disease", FEBS Letters, 579: 1338-1342, 2005.

Stewart "Theoretical Aspects of Antibiotic Diffusion Into Microbial Biofilms", Antimicrobial Agents and Chemotherapy, 40(11): 2517-2522, 1996.

Toledano et al. "Enzyme-Triggered Self-Assembly of Peptide Hydrogels Via Reversed Hydrolysis", Journal of the American Chemical Society, JACS, XP002421984, 128(4): 1070-1071, Feb. 1, 2006.

True et al. "Epigenetic Regulation of Trenslation Reveals Hidden Genetic Variation to Produce Complex Traits", Nature, 431: 184-187, 2004.

Tsai et al. "Synthesis of AIB-Containing Peptidomimetics as Potential Inhibitors of Alzheimer's Gamma-Secretase", 218th ACS National Meeting, New Orleans, USA, Meeting Abstract, MEDI-018, 1999. Abstract.

Tsang et al. "A Simple Chemical Method of Opening and Filling Carbon Nanotubes", Nature, 372: 159-162, 1994.

Tuitc ct al. "Propagation of Yeast Prions", Nature Reviews, 4: 878-889, 2003.

Vauthey et al. "Molecular Self-Assembly of Surfactant-Like Peptides to Form Nanotubes and Nanovesicles", Proc. Natl. Acad. Sci. USA, 99(8): 5355-5360, 2002.

Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.

Yan et al. "Self-Assembling and Application of Diphenylalanine-Based Nanostructures", Chemical Society Reviews, 39: 1877-1890, 2010.

Yokoi et al. "Dynamic Reassembly of Peptide RADA16 Nanofiber Scaffold", Proc. Natl. Acad. Sci. USA, XP002446152, 102(24): 8414-8419, Jun. 2005.

Zhang "Fabrication of Novel Biomaterials Through Molecular Self-Assembly", Nature Biotechnology, XP002305982, 21(10): 1171-1178, Oct. 1, 2003. p. 1172-1173, p. 1173, Right Col., p. 1174.

Zhang et al. "Design of Nanostructured Biological Materials Through Self-Assembly of Peptides and Proteins", Current Opinion in Chemical Biology, 6: 865-871, 2002.

Zhang et al. "Supramolecular Hydrogels Respond to Ligand-Receptor Interaction", Journal of the American Chemical Society, XP002421981, 125(45): 13680-13681, Nov. 12, 2003.

Zhao et al. "Fabrication of Molecular Materials Using Peptide Construction Motifs", Trends in Biotechnology, XP004552612, 22(9): 470-476, Sep. 1, 2004.

Official Action Dated Sep. 24, 2015 From the US Patent and Trademark Office Re. U.S. Appl. No. 12/083,222.

* cited by examiner

METHOD OF FORMING A FIBER MADE OF PEPTIDE NANOSTRUCTURES

RELATED APPLICATIONS

This application is a division of U.S. patent application Ser. No. 11/659,150 filed on Oct. 17, 2008, which is a National Phase of PCT Patent Application No. PCT/IL2005/000589 having International Filing Date of Jun. 5, 2005, which claims the benefit of priority of U.S. Provisional Patent Application No. 60/592,523 filed on Aug. 2, 2004. The contents of the above applications are all incorporated herein by reference.

FIELD AND BACKGROUND OF THE INVENTION

The present invention relates to articles made of nanostructures and, more particularly, to articles made of peptide nanostructures having sizes at least in the micrometer scale.

Material sciences involve the understanding of material characteristics as well as the development of new materials. Industrial and academic needs encourage material scientists to develop new materials having superior mechanical, electrical, optical and/or magnetic properties for many applications. Modern material sciences focus on the investigation of polymers, ceramics and semiconductors in many fluidic as well as solid forms including fibers, thin films, material bulks and the like.

Various manufacturing processes are known in the art for making synthetic fibers. Many synthetic fibers are produced by extrusion processes, in which a thick viscous liquid polymer precursor or composition is forced through one or more tiny holes of a spinneret to form continuous filaments of semi-solid polymer. As the filaments emerge from the holes of a spinneret, the liquid polymer converts first to a rubbery state which then is solidified. The process of extruding and solidifying filaments is generally known as spinning.

Wet spinning processes are typically employed with fiber-forming substances that have been dissolved in a solvent. Wet spinning techniques are preferred for spinning of high molecular weight polyamides. The spinnerets forming the filaments are submerged in a wet chemical bath, and as the filaments of the fiber-forming substances emerge from the spinnerets, they are induced to precipitate out of the solution and solidify.

In gel spinning, the polymer is not in a true liquid state during extrusion. The polymer chains are bound together at various points in liquid crystal form. This produces strong inter-chain forces in the resulting filaments that can significantly increase the tensile strength of the fibers. In addition, the liquid crystals are aligned along the fiber axis by the shear forces during extrusion. The filaments emerge with high degree of orientation relative to each other, further enhancing the strength. Typically, in gel spinning, the filaments first pass through air and then cooled in a liquid bath.

In dry spinning, the polymer is dissolved in a volatile solvent and the solution is pumped through the spinneret. As the fibers exit the spinneret, air is used to evaporate the solvent such that the fibers solidify and can be collected on a take-up wheel.

In melt spinning the polymer is melted and pumped through the spinneret. The molten fibers are cooled, solidified, and collected on a take-up wheel. Stretching of the fibers in both the molten and solid states provides for orientation of the polymer chains along the fiber axis.

Dispersion spinning is typically employed when the polymer having and infusible, insoluble and generally intractable characteristics. In this technique, the polymer is dispersed as fine particles in a chemical carrier that permit extrusion into fiber. The dispersed polymer is then caused to coalesce by a heating process and the carrier is removed by a thermal or chemical procedure.

Reaction spinning processes involve the formation of filaments from pre-polymers and monomers. The pre-polymers and monomers are further polymerized and cross-linked after the filament is formed. The reaction spinning process begins with the preparation of a viscous spinning solution, which is prepared by dissolving a low molecular weight polymer in a suitable solvent and a reactant. The spinning solution is then forced through the spinneret into a solution or being combined with a third reactant. The primary distinguishable characteristic of reaction spinning processes is that the final cross-linking between the polymer molecule chains in the filament occurs after the fibers have been spun. Post-spinning steps typically include drying and lubrication.

In tack spinning, a polymeric material in a tacky state is interposed between a foundation layer and a temporary anchorage surface. Being in a tacky state, the polymeric material adheres to the foundation layer and the temporary anchorage surface. The foundation layer is then separated from the temporary anchorage surface to produce fibers of the polymeric material. The fibers are hardened by thermal or chemical treatment, and separated from the temporary anchorage surface.

In electrospinning, a fine stream or jet of liquid is produced by pulling a small amount of charged liquefied polymer through space using electrical forces. The produced fibers are hardened and collected on a suitably located precipitation device to form a nonwoven article. In the case of a liquefied polymer which is normally solid at room temperature, the hardening procedure may be mere cooling, however other procedures such as chemical hardening or evaporation of solvent may also be employed.

Other processes for manufacturing polymeric articles include film blowing and injection molding.

In film blowing, an extruder is used to melt the polymer and pump it into a tubular die. Air blown into the center of the tube causes the melt to expand in the radial direction. The melt in thus extended in both radial and down-stream direction. The formed film is then collected by an arrangement of rollers.

In injection molding, a reciprocating or rotating screw both melts polymer pellets and provides the pressure required to inject the melt into a cold mold. The cold mold provides the article the desired shape.

In the area of thin film production, a well-known method for producing and depositing monolayers is the Langmuir-Blodgett method. In this method a monolayer of amphiphilic molecules is formed at the surface of a tank filled with a liquid sub-phase such as water. Amphiphilic molecules are those having a hydrophobic first end and a hydrophilic second end lined up side by side in a particular direction. In the Langmuir-Blodgett method, a solution of amphiphilic molecules dissolved in a solvent which is not miscible with the sub-phase liquid in the tank is spread onto the liquid surface. When the solvent evaporates, a loosely packed monolayer is formed on the surface of the sub-phase. A transition of the monolayer thus formed from a state of gas or liquid to a solid state is then achieved by compressing surface area of the layer to a predetermined surface pressure. The resulting monolayer is deposited onto the surface of a substrate by passing the substrate through the compressed layer while maintaining the layer at a predetermined surface pressure during the period of deposition.

Another method for producing a monolayer is known as self-assembling of molecules. In this method, a monolayer film is generated as a result of adsorption and bonding of suitable molecules (e.g., fatty acids, organic silicon molecules or organic phosphoric molecules) on a suitable substrate surface. The method typically involves solution deposition chemistry in the presence of water.

Over the years, extensive efforts were made to develop row materials which can be used for manufacturing fiber and films by the above techniques to provide articles having enhanced and/or application-specific characteristics. For example, one of the most studied natural fibrillar system is silk [Kaplan D L, "Fibrous proteins—silk as a model system," Polymer degradation and stability, 59:25-32, 1998]. There are many forms of silk, of which spider silk of *Nephila clavipas* (the golden orb weaver) is regarded as nature's high performance fiber, with a remarkable combination of strength, flexibility, and toughness. Although assembled by non-covalent interactions, silk is stronger than steel per given fibrillar diameter but, at the same time, is much more flexible. Due to its superior mechanical properties, the spider silk can be used in many areas requiring the combination of high mechanical strength with biodegradability, e.g., in tissue engineering applications [Kubik S., "High-Performance Fibers from Spider Silk," Angewandte Chemie International Edition, 41:2721-2723, 2002].

A known method of synthesizing spider silk material includes the introduction of a spider silk gene into a heterologous gene expression system and the secretion of spider silk protein therefrom. The protein is then processed, typically by electrospinning, to produce a fiber of enhanced mechanical properties [Jin H J, Fridrikh S V, Rutledge G C and Kaplan D L, "Electrospinning *Bombyx mori* silk with poly(ethylene oxide)," Biomacromolecules, 3:1233-1239, 2002].

Recently, electrospinning has been employed to fabricate virus-based composite fibers hence to mimic the spinning process of silk spiders [Lee S and Belcher A M, "Virus-Based Fabrication of Micro- and Nanofibers Using Electrospinning," Nano letters, 4:388-390, 2004]. In this study, M13 virus was genetically modified to bind conductive and semiconductor materials, and was thereafter subjected to an electrospinning process to provide conductive and semiconductor fibers.

Other than synthesized spider silk, the electrospinning process can be applied on a diversity of polymers including polyamides, polyactides and water soluble polymer such as polyethyleneoxide [Huang Z M, Zhang Y Z, Kotaki M and Ramakrishna S., "A review on polymer nanofibers by electrospinning and their applications in nanocomposites," Composites Science and technology, 63:2223-2253, 2003]. Heretofore, about 50 types of polymers have been successfully electrospun.

Electrospinning has also been used with carbon nanotubes to obtain super-though carbon-nanotube fibers [Dalton A B et al., "Super-tough carbon-nanotube fibres—These extraordinary composite fibres can be woven into electronic textiles," Nature, 423:703, 2003]. By modifying a familiar method for carbon nanotubes fibers [Vigolo et al., "Macroscopic Fibers and Ribbons of Oriented Carbon Nanotubes," Science, 17:1331-1334, 2000] the researchers were able to spin a reel of nanotube gel fiber and then convert it into 100 m length of solid nanotube composite fiber. The resulting fibers were tougher than any other known natural or synthetic organic fiber.

However, carbon nanotubes in general and carbon-nanotube fibers in particular suffer from structural deviations. Although deviations in structure can be introduced in a "controlled" manner under specific conditions, frequent uncontrollable insertion of such defects result in spatial structures with unpredictable electronic, molecular and structural properties. In addition, the production process of carbon nanotubes is very expensive and presently stands hundreds of U.S. dollars per gram.

Other known nanostructures are peptide-based nanotubular structures, made through stacking of cyclic D-, L-peptide subunits. These peptides self-assemble through hydrogen-bonding interactions into nanotubules, which in-turn self-assemble into ordered parallel arrays of nanotubes. The number of amino acids in the ring determines the inside diameter of the nanotubes obtained. Such nanotubes have been shown to form transmembrane channels capable of transporting ions and small molecules [Ghadiri, M. R. et al., Nature 366, 324-327 (1993); Ghadiri, M. R. et al., Nature 369, 301-304 (1994); Bong, D. T. et al., Angew. Chem. Int. Ed. 40:988-1011, 2001].

More recently, surfactant-like peptides that undergo spontaneous assembly to form nanotubes with a helical twist have been discovered. The monomers of these surfactant peptides, like lipids, have distinctive polar and nonpolar portions. They are composed of 7-8 residues, approximately 2 nm in length when fully extended, and dimensionally similar to phospholipids found in cell membranes. Although the sequences of these peptides are diverse, they share a common chemical property, i.e., a hydrophobic tail and a hydrophilic head. These peptide nanotubes, like carbon and lipid nanotubes, also have a very high surface area to weight ratio. Molecular modeling of the peptide nanotubes suggests a possible structural organization [Vauthey (2002) Proc. Natl. Acad. Sci. USA 99:5355; Zhang (2002) Curr. Opin. Chem. Biol. 6:865]. Based on observation and calculation, it is proposed that the cylindrical subunits are formed from surfactant peptides that self-assemble into bilayers, where hydrophilic head groups remain exposed to the aqueous medium. Finally, the tubular arrays undergo self-assembly through non-covalent interactions that are widely found in surfactant and micelle structures and formation processes.

Peptide based bis(N-α-amido-glycyglycine)-1,7-heptane dicarboxylate molecules were also shown to be assembled into tubular structures [Matsui (2000) J. Phys. Chem. B 104: 3383].

When the crystal structure of di-phenylalanine peptides was determined, it was noted that hollow nanometric channels are formed within the framework of the macroscopic crystal [Gorbitz et al., Chemistry 7(23):5153-9, 2001]. However, no individual nanotubes could be formed by crystallization, as the crystallization conditions used in this study included evaporation of an aqueous solution at 80° C. No formation of discrete nano-structures was reported under these conditions.

International Patent Application Nos. IL03/01045 and IL2004/000012 (see also Reches M and Gazit E, "Casting metal nanowires within discrete self-assembled peptide nanotubes," Science, 300:625-627, 2003), disclose a new procedure for making peptide nanostructures that show many ultrastructural and physical similarities to carbon nanotubes. These peptide nanostructures are self assembled by diphenylalanine, the core recognition motif of the β-amyloid peptide [Findeis et al., "Peptide inhibitors of beta amyloid aggregation," Biochemistry, 38:6791, 1999; Tjernberg et al., "Arrest of -Amyloid Fibril Formation by a Pentapeptide Ligand," J. Biol. Chem., 271:8545-8548, 1996; and Soto et al., "Beta-sheet breaker peptides inhibit fibrillogenesis in a rat brain model of amyloidosis: implications for Alzheimer's therapy," Nature Medicine, 4:822-826, 1998].

The self-assembled peptide nanostructures are well ordered assemblies of various shapes with persistence length on the order of micrometers. The formation of the peptide nanostructures is very efficient and the nanostructures solution is very homogeneous. Similar to carbon nanotubes, the peptide nanostructures are formed as individual entities. For industrial applications, the self-assembled peptide nanostructures are favored over carbon nanotubes and spider silk from standpoint of cost, production means and availability.

There is thus a widely recognized need for, and it would be highly advantageous to have macroscopic and microscopic articles exploiting the advantages of self-assembled peptide nanostructures.

SUMMARY OF THE INVENTION

According to one aspect of the present invention there is provided a method of forming a fiber made of peptide nanostructures, the method comprising providing peptide nanostructures in solution, and fiberizing the solution thereby forming at least one fiber of the peptide nanostructures.

According to further features in preferred embodiments of the invention described below, the fiberizing is by an electrospinning process, a wet spinning process, a dry spinning process, a gel spinning process, a dispersion spinning process, a reaction spinning process or a tack spinning process.

According to another aspect of the present invention there is provided a method of forming a film of peptide nanostructures, comprising: dissolving peptide molecules in an organic solvent; adding an aqueous solvent to the organic solvent such that an interface is formed between the organic solvent and the aqueous solvent; and incubating the organic and the aqueous solvents under conditions which allow the peptide molecules to form a film of peptide nano structures in the interface.

According to still further features in the described preferred embodiments the organic solvent is an aromatic solvent, such as but not limited to benzene. According to still further features in the described preferred embodiments the hydrophilic solvent is water.

According to yet another aspect of the present invention there is provided a method of forming at least one layer of peptide nanostructures, comprising: placing peptide nanostructures in an organic solvent; applying at least one droplet of the organic solvent onto a surface of an hydrophilic solvent; and applying pressure onto the at least one droplet of the organic solvent, so as to form at least one layer of peptide nanostructures on the surface of the hydrophilic solvent.

According to further features in preferred embodiments of the invention described below, the method further comprises transferring the at least one layer of the peptide nanostructures to a substrate.

According to still further features in the described preferred embodiments the transferring of the layer(s) to the substrate is effected by a Langmuir-Blodgett technique or a Langmuir-Schaeffer technique.

According to still another aspect of the present invention there is provided a method of forming an aligned array or film of peptide nanostructures. The method comprising: dissolving peptide molecules in an organic solvent; applying the organic solvent on a substrate; and incubating the substrate and the organic solvent under conditions which allow the peptide molecules to form an aligned array or a film of peptide nanostructures on the substrate.

According to further features in preferred embodiments of the invention described below, the nanostructures are responsive to a magnetic field. According to still further features in the described preferred embodiments the method further comprises subjecting the substrate to a magnetic field.

According to further features in preferred embodiments of the invention described below, the nanostructures are responsive to an electric field. According to still further features in the described preferred embodiments the method further comprises subjecting the substrate to an electric field.

According to still another aspect of the present invention there is provided a method of forming a fiber made of peptide nanostructures, the method comprising subjecting peptide nanostructures, in solution, to an electric field so as to form at least one fiber of the peptide nanostructures.

According to further features in preferred embodiments of the invention described below, collecting the at least one fiber on a precipitation electrode.

According to still further features in the described preferred embodiments the collecting of the fiber(s) comprises rotating the precipitation electrode so as to wind the at least one fiber around the precipitation electrode.

According to still further features in the described preferred embodiments the collecting of the fiber(s) comprises moving the at least one fiber relative to the precipitation electrode so as to provide a nonwoven mat of peptide nanostructures.

According to still further features in the described preferred embodiments the method further comprises unwinding the at least one fiber of the peptide nanostructure off the precipitation electrode.

According to an additional aspect of the present invention there is provided a fiber comprising a plurality of peptide nanostructures as described herein, the fiber being at least 100 nm in length.

According to still an additional aspect of the present invention there is provided a nonwoven article comprising a plurality of electrospun fibers, wherein at least one of the plurality of electrospun fibers is the fiber described herein.

According to yet a further aspect of the present invention there is provided a thin film comprising at least one layer of peptide nanostructures as described herein, the thin film being at least 100 $nm^2$ in area size.

According to further features in preferred embodiments of the invention described below, each of the peptide nanostructures comprises no more than 4 amino acids, at least one of the 4 amino acids being an aromatic amino acid.

According to still further features in the described preferred embodiments each of the 4 amino acids is independently selected from the group consisting of naturally occurring amino acids, synthetic amino acids, β-amino acids, Peptide Nucleic Acid (PNA) and combinations thereof.

According to still further features in the described preferred embodiments at least one of the 4 amino acids is a D-amino acid.

According to still further features in the described preferred embodiments at least one of the 4 amino acids is an L-amino acid.

According to still further features in the described preferred embodiments at least one of the peptide nanostructures comprises at least two aromatic moieties.

According to still further features in the described preferred embodiments at least one of the peptide nanostructures is a homodipeptide.

According to still further features in the described preferred embodiments each of the amino acids is the homodipeptide comprises an aromatic moiety, such as, but not limited to, substituted naphthalenyl, unsubstituted naphthalenyl, substituted phenyl or unsubstituted phenyl.

According to still further features in the described preferred embodiments the substituted phenyl is selected from the group consisting of pentafluoro phenyl, iodophenyl, biphenyl and nitrophenyl.

Thus, representative examples of the amino acids in the homopeptide include, without limitation, naphthylalanine, p-nitro-phenylalanine, iodo-phenylalanine and fluoro-phenylalanine.

According to still further features in the described preferred embodiments the homodipeptide is selected from the group consisting of naphthylalanine-naphthylalanine dipeptide, (pentafluoro-phenylalanine)-(pentafluoro-phenyl alanine)dipeptide, (iodo-phenylalanine)-(iodo-phenylalanine) dipeptide, (4-phenyl phenylalanine)-(4-phenyl phenylalanine)dipeptide and (p-nitro-phenylalanine)-(p-nitro-phenylalanine)dipeptide.

According to still further features in the described preferred embodiments each of the peptide nanostructures comprises a plurality of polyaromatic peptides.

According to still further features in the described preferred embodiments each of the plurality of polyaromatic peptides comprises a component selected from the group consisting of a polyphenylalanine peptide, a polytriptophane peptide, a polytyrosine peptide, a non-natural derivatives thereof and a combination thereof.

According to still further features in the described preferred embodiments each of the plurality of polyaromatic peptides comprises at least 30 amino acids.

According to still further features in the described preferred embodiments the nanostructures at least partially enclose a material therein.

According to still further features in the described preferred embodiments the material is in a gaseous state.

According to still further features in the described preferred embodiments the material is in a condensed state.

According to still further features in the described preferred embodiments the material is selected from the group consisting of a conducting material, a semiconducting material, a thermoelectric material, a magnetic material, a light-emitting material, a biomineral, a polymer and an organic material.

According to still further features in the described preferred embodiments the conducting material is selected from the group consisting of silver, gold, copper, platinum, nickel and palladium.

According to still further features in the described preferred embodiments the semiconducting material is selected from the group consisting of CdS, CdSe, ZnS and $SiO_2$.

According to still further features in the described preferred embodiments the magnetic material is a paramagnetic material.

According to still further features in the described preferred embodiments the paramagnetic material is selected from the group consisting of cobalt, copper, nickel and platinum.

According to still further features in the described preferred embodiments the magnetic material is a ferromagnetic material.

According to still further features in the described preferred embodiments the ferromagnetic material is selected from the group consisting of magnetite and NdFeB.

According to still further features in the described preferred embodiments the light-emitting material is selected from the group consisting of dysprosium, europium, terbium, ruthenium, thulium, neodymium, erbium, ytterbium and any organic complex thereof.

According to still further features in the described preferred embodiments the biomineral comprises calcium carbonate.

According to still further features in the described preferred embodiments the polymer is selected from the group consisting of polyethylene, polystyrene polyvinyl chloride and a thermoplastic polymer.

According to still further features in the described preferred embodiments the thermoelectric material is selected from the group consisting of bismuth telluride, bismuth selenide, bismuth antimony telluride and bismuth selenium telluride.

According to still further features in the described preferred embodiments the polymer is selected from the group consisting of a polynucleotide and a polypeptide.

The present invention successfully addresses the shortcomings of the presently known configurations by providing a fiber, film, article and method of manufacturing the same. The fiber, film, article and method of the present invention enjoy properties far exceeding the prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
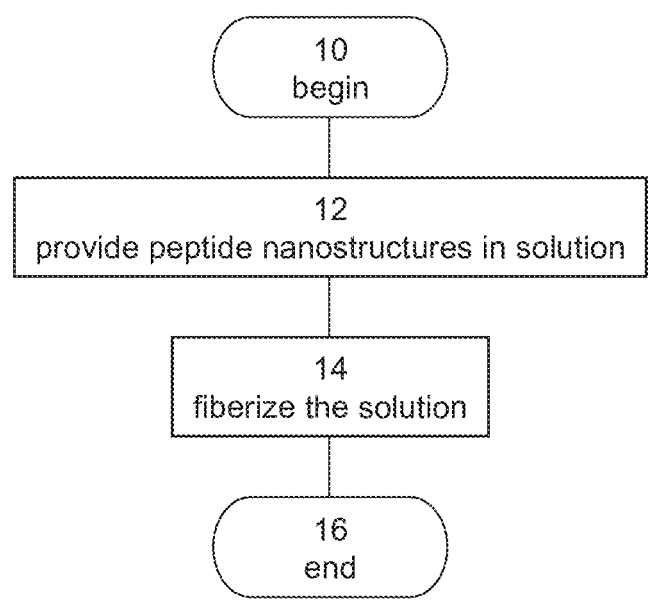
FIG. 1 is a flowchart diagram of a method suitable for forming a fiber made of peptide nanostructures, according to a preferred embodiment of the present invention.

The present invention is of a method which can be used for manufacturing articles of peptide nanostructures. Specifically, the present invention can be used to manufacture fibers, films and other articles having sizes at least in the micrometer scale. The present invention is further of fibers, films and other articles made of peptide nanostructures.

The principles and operation of a method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 is a flowchart diagram of a method suitable for forming a fiber made of peptide nanostructures. The method begins at step 10 and continues to step 12 in which peptide nanostructures in solution are provided.

As used herein the phrase "nanostructure" refers to a structure having a diameter or a cross-section of less than 1 μm (preferably less than 500 nm, more preferably less than about 50 nm, even more preferably less than about 5 nm). The length of the nanostructure of the present embodiments is preferably at least 1 nm, more preferably at least 10 nm, even more preferably at least 100 nm and even more preferably at least 500 nm. It will be appreciated, though, that the nanostructure of the present embodiments can be of infinite length (i.e., macroscopic fibrous structures) and as such can be used in the fabrication of hyper-strong materials.

As used herein the term "about" refers to ±10%.

The solution can be prepared, for example, by placing or dissolving the nanostructures in an organic solvent, which is preferably an aromatic solvent, such as, but not limited to, benzene. Additionally, the solution may contain polymeric additives, or any other material suitable for forming fibers therefrom.

The method continues to step 14 in which the solution is fiberized to form at least one fiber of peptide nanostructures.

The solution can be fiberized by any conventional process, such as, but not limited to, a spinning process, a blowing process, an injection process and the like. Contemplated spinning processes include, without limitation, wet spinning process, gel spinning process, dry spinning process, dispersion spinning process, reaction spinning process, tack spinning process and electrospinning process. These spinning processes are described in the Background section above and can be found in many text books and patents, see, e.g., U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference. Representative examples of spinning processes in various preferred embodiments of the present invention are further detailed hereinunder.

The method ends at step 16.

Peptide nanostructures which can be used according to the present embodiments include nanostructures composed of surfactant like peptides and cyclic D-, L-peptide subunits. The nanostructures can be self-assembled from a plurality of peptides. Preferably, but not obligatorily, the peptides include no more than 4 amino acids of which at least one is an aromatic amino acid.

In various exemplary embodiments of the embodiments the peptides comprise a dipeptide or a tripeptide. The shape of the nanostructures depends on the rigidity of the molecular structure of the peptide used. For example a plurality of diphenylglycine peptides which offer similar molecular properties as diphenylalenine peptides albeit with a lower degree of rotational freedom around the additional C—C bond and a higher steric hindrence self-assemble into nano-spheres, while a plurality of diphenylalenine peptides self-assemble into nano-tubes.

The present embodiments also envisages nanostructures which are composed of a plurality of polyaromatic peptides being longer than the above described (e.g., 50-136 amino acids).

As used herein the phrase "polyaromatic peptides" refers to peptides which include at least 80%, at least 85% at least 90%, at least 95% or more, say 100% aromatic amino acid residues. These peptides can be homogenic (e.g., polyphenylalanine) or heterogenic of at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 120, at least 125, at least 130, at least 135, at least 140, at least 145, at least 150, at least 155, at least 160, at least 170, at least 190, at least 200, at least 300 or at least 500 amino acids.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylalanine (Nal), ring-methylated derivatives of Phe, halogenated derivatives of Phe or O-methyl-Tyr and β amino-acids In addition to the above, the peptides of the present embodiments may also include one or more modified amino acids (e.g., thiolated or biotinylated amino acids) or one or more non-amino acid monomers (e.g., fatty acids, complex carbohydrates etc.). Also contemplated are homodipeptides, and more preferably aromatic homodipeptides in which each of the amino acids comprises an aromatic moiety, such as, but not limited to, substituted or unsubstituted naphthalenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thioalkoxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydro furane, tetrahydropyrane, morpholino and the like.

A "hydroxy" group refers to an —OH group.

An "azide" group refers to a —N=N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to an —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" group refers to fluorine, chlorine, bromine or iodine.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

Figure 8:
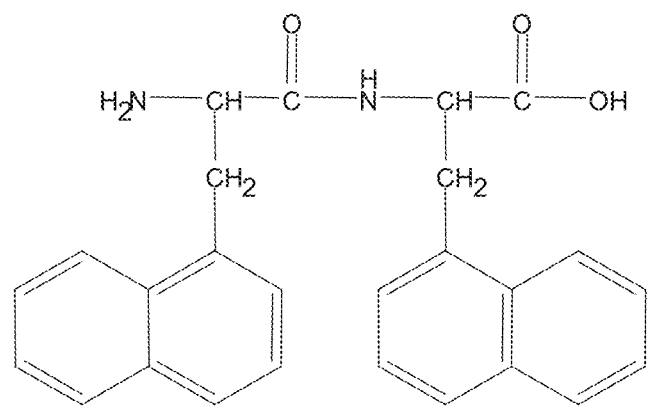
FIG. 8 is a schematic illustration of a chemical structure of a naphthylalanine-naphthylalanine (Nal-Nal) dipeptide.
Figure 9:
FIG. 9 is an electron microscope image of Nal-Nal tubular nanostructures.

Representative examples of homodipeptides which can be used include, without limitation, naphthylalanine-naphthylalanine (nal-nal), (pentafluoro-phenylalanine)-(pentafluoro-phenylalanine), (iodo-phenylalanine)-(iodo-phenylalanine), (4-phenyl phenylalanine)-(4-phenyl phenylalanine) and (p-nitro-phenylalanine)-(p-nitro-phenylalanine), see Examples 4, 5 and FIGS. 8-10.

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The nanostructures which can be used in the present embodiments are preferably generated by allowing a highly concentrated hydrophilic solution of the peptides of the present embodiments to self-assemble under mild conditions. The resulting nanostructures are preferably stable under acidic and/or basic pH conditions, a wide range of temperatures (e.g., 4-400° C., more preferably 2-200° C.) and/or proteolytic conditions (e.g., proteinase K).

It was found by the present Inventor that the peptide nanostructures are sufficiently stable to allow integration of the peptide nanostructures into polymer fibers during manufacturing process of fibers or other articles.

Depending on the number and type of amino acids used, the nanostructure can be insulators, conductors or semiconductors. The nanostructure of the present embodiments can also be utilized as carriers onto which atoms of different materials (e.g., conductive materials, chemical or biological agents, etc.) may be incorporated.

According to preferred embodiments of the present invention, the nanostructures are filled or partially filled with at least one material (i.e., the nanostructures enclose or partially enclose the material). The material can be composed of a conducting material, a semiconducting material, a thermoelectric material, a magnetic material (paramagnetic, ferromagnetic or diamagnetic), a light-emitting material, a gaseous material, a biomineral, a polymer and/or an organic material.

For example, the nanostructures may enclose conducting or semiconducting materials, including, without limitation, inorganic structures such as Group IV, Group III/Group V, Group II/Group VI elements, transition group elements, or the like.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po.

Thus, for conducting materials, the nanostructures may enclose, for example, silver, gold, copper, platinum, nickel or palladium. For semiconducting materials the nanostructures may enclose, for example, silicon, indium phosphide, gallium nitride and others.

The nanostructures may also encapsulate, for example, any organic or inorganic molecules that are polarizable or have multiple charge states. For example, the nanostructures may include main group and metal atom-based wire-like silicon, transition metal-containing wires, gallium arsenide, gallium nitride, indium phosphide, germanium, or cadmium selenide structures.

Additionally, the nanostructure of the present embodiments may enclose various combinations of materials, including semiconductors and dopants. Representative examples include, without limitations, silicon, germanium, tin, selenium, tellurium, boron, diamond, or phosphorous. The dopant may also be a solid solution of various elemental semiconductors, for example, a mixture of boron and carbon, a mixture of boron and P, a mixture of boron and silicon, a mixture of silicon and carbon, a mixture of silicon and germanium, a mixture of silicon and tin, or a mixture of germanium and tin. In some embodiments, the dopant or the semiconductor may include mixtures of different groups, such as, but not limited to, a mixture of a Group III and a Group V element, a mixture of Group III and Group V elements, a mixture of Group II and Group VI semiconductors. Additionally, alloys of different groups of semiconductors may also be possible, for example, a combination of a Group II-Group VI and a Group III-Group V semiconductor and a Group I and a Group VII semiconductor.

Specific and representative examples of semiconducting materials which can be encapsulated by the nanostructure of the present embodiments include, without limitation, CdS, CdSe, ZnS and $SiO_2$.

The nanostructure of the present embodiments may also enclose a thermoelectric material that exhibits a predetermined thermoelectric power. Preferably, such a material is selected so that the resulting nanostructure composition is characterized by a sufficient figure of merit. Such composition may be used in thermoelectric systems and devices as heat transfer media or thermoelectric power sources. According to a preferred embodiment of the present invention the thermoelectric material which can be encapsulated in the nanostructure of the present embodiments may be a bismuth-based material, such as, but not limited to, elemental bismuth, a bismuth alloy or a bismuth intermetallic compound. The thermoelectric material may also be a mixture of any of the above materials or other materials known to have thermoelectric properties. In addition the thermoelectric material may also include a dopant. Representative examples include, without limitation, bismuth telluride, bismuth selenide, bismuth antimony telluride, bismuth selenium telluride and the like. Other materials are disclosed, for example, in U.S. Patent Application No. 20020170590.

As stated, the nanostructure of the present embodiments may also enclose magnetic materials. Generally, all materials in nature posses some kind of magnetic properties which are manifested by a force acting on a specific material when present in a magnetic field. These magnetic properties, which originate from the sub-atomic structure of the material, are different from one substrate to another. The direction as well as the magnitude of the magnetic force is different for different materials.

Whereas the direction of the force depends only on the internal structure of the material, the magnitude depends both on the internal structure as well as on the size (mass) of the material. The internal structure of the materials in nature, to which the magnetic characteristics of matter are related, is classified according to one of three major groups: diamagnetic, paramagnetic and ferromagnetic materials, where the strongest magnetic force acts on ferromagnetic materials.

In terms of direction, the magnetic force acting on a diamagnetic material is in opposite direction than that of the magnetic force acting on a paramagnetic or a ferromagnetic material. When placed in external magnetic field, a specific material acquires a non-zero magnetic moment per unit volume, also known as a magnetization, which is proportional to the magnetic field vector. For a sufficiently strong external magnetic field, a ferromagnetic material, due to intrinsic non-local ordering of the spins in the material, may retain its magnetization, hence to become a permanent magnet. As opposed to ferromagnetic materials, both diamagnetic and paramagnetic materials loose the magnetization once the external magnetic field is switched off.

Representative examples of paramagnetic materials which can be enclosed by the nanostructure of the present embodiments include, without limitation, cobalt, copper, nickel and platinum. Representative examples of ferromagnetic materials include, without limitation, magnetite and NdFeB.

Other materials which may be encapsulated by the nanostructure of the present embodiments include, without limitation, light-emitting materials (e.g., dysprosium, europium, terbium, ruthenium, thulium, neodymium, erbium, ytterbium or any organic complex thereof), biominerals (e.g., calcium carbonate), polymers (e.g., polyethylene, polystyrene, polyvinyl chloride, polynucleotides and polypeptides, thermoplastics, fluorescent materials or other colored materials.

In order to generate the filled nanostructure of the present embodiments, the foreign material is introduced into the internal cavity of the nanostructure, to encapsulate the material in nanostructure.

Exemplified methods for filling nanostructure are described in "Capillarity-induced filling of carbon nanotubes", P M Ajayan et al., Nature, vol. 361, 1993, pp. 333-334; "A simple chemical method of opening and filling carbon nanotubes", SC Tsang et al., Nature, vol. 372, 1994, pp. 159-162; and U.S. Pat. Nos. 5,916,642 and 6,361,861.

Following are representative examples of spinning methods which can be used in various preferred embodiments of the present invention.

In the embodiment in which electrospinning is employed, the solution with the peptide nanostructures is extruded, for example under the action of hydrostatic pressure, through capillary apertures of a dispenser, which is spaced apart from a precipitation electrode. The dispenser and precipitation electrode are kept at different electrical potentials thus forming an electric field therebetween. Under the effect of electrical force, jets depart from the dispenser and travel towards the precipitation electrode. Moving with high velocity in the inter-electrode space, the jet cools or solvent therein evaporates, thus forming fibers which are collected on the surface of the precipitation electrode.

In the embodiment in which a wet spinning process is employed, the solution with the peptide nanostructure of the present embodiments is extruded through a spinneret, under the action of mechanical forces (e.g., pressure, gravity). The formed fiber(s) can then be collected using a suitable take up device, e.g., a drum.

In the embodiment in which a dry spinning process is employed, the solution with the peptide nanostructures of the present embodiments is extruded through a spinneret, and solvent therein is rapidly evaporated by inert gas. Similarly to the above, the formed fiber(s) can be collected using a take up device.

In the embodiment in which tack spinning is employed, the solution is preferably prepared in a tack state. This can be done, for example, by mixing the solution with certain polymeric additives which facilitate the adherence of the solution to a surface. Once prepared, the solution with the peptide nanostructures is pressed against a heated surface, such as, but not limited to, a heated roll. The solution can then be separated from the surface and cooled by blowing cold air or another cooling medium into a nip formed between the heated surface and the solution as the solution is separated from the surface. The separation and cooling of the solution result in drawing of fibrils out from the surface.

In any event, once the fibers are formed and collected, they can be unwound off the take up device, if desired, for example, for packing or storage purposes or for uploading to another apparatus.

It is expected that during the life of this patent many relevant spinning processes will be developed and the scope of the term spinning processes is intended to include all such new technologies a priori.

Performing the above method according to present embodiments successfully produces one or more fibers. Therefore, according to another aspect of the present invention there is provided a fiber of peptide nanostructures. In accordance with preferred embodiments of the present invention the fiber is at least 100 nm, more preferably at least 1 µm, more preferably at least 10 µm in length. The fiber can contain any of the aforementioned peptide nanostructures.

The fibers of the present embodiments can be used for forming nonwoven articles. This can be done, for example, by repeating the selected spinning process a plurality of times and allowing the formed fiber to precipitate on a suitable precipitation device thus forming the nonwoven article thereupon. As will be appreciated by one ordinarily skilled in the art, when a relative motion is established between the formed fiber(s) and the precipitation device, a nonwoven mat of fibers made of peptide nanostructures is formed.

Figure 2:
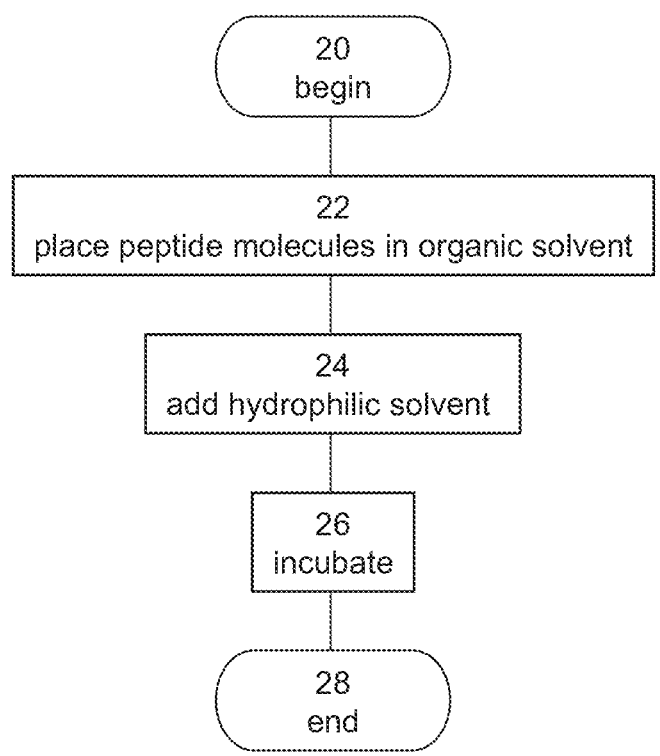
FIG. 2 is a flowchart diagram of a method suitable for forming a film of peptide nanostructures, according to a preferred embodiment of the present invention.

Reference is now made to FIG. 2 which is a flowchart diagram of a method suitable for forming a film of peptide nanostructures, according to a preferred embodiment of the present invention. The method begins at step 20 and continues to step 22 in which peptide molecule are placed in an organic solvent. The method continues to step 24 in which an hydrophilic solvent (e.g., water) is added to the organic solvent, such that an interface is formed between the organic and hydrophilic solvents. The method then proceeds to step 26 in which the organic and hydrophilic solvents are incubated under conditions which allow the peptide molecules to form a film of peptide nanostructures in the formed interface. The incubation conditions are such that the nanostructures are self-assembled as further detailed hereinabove.

The method ends at step 28.

Figure 3:
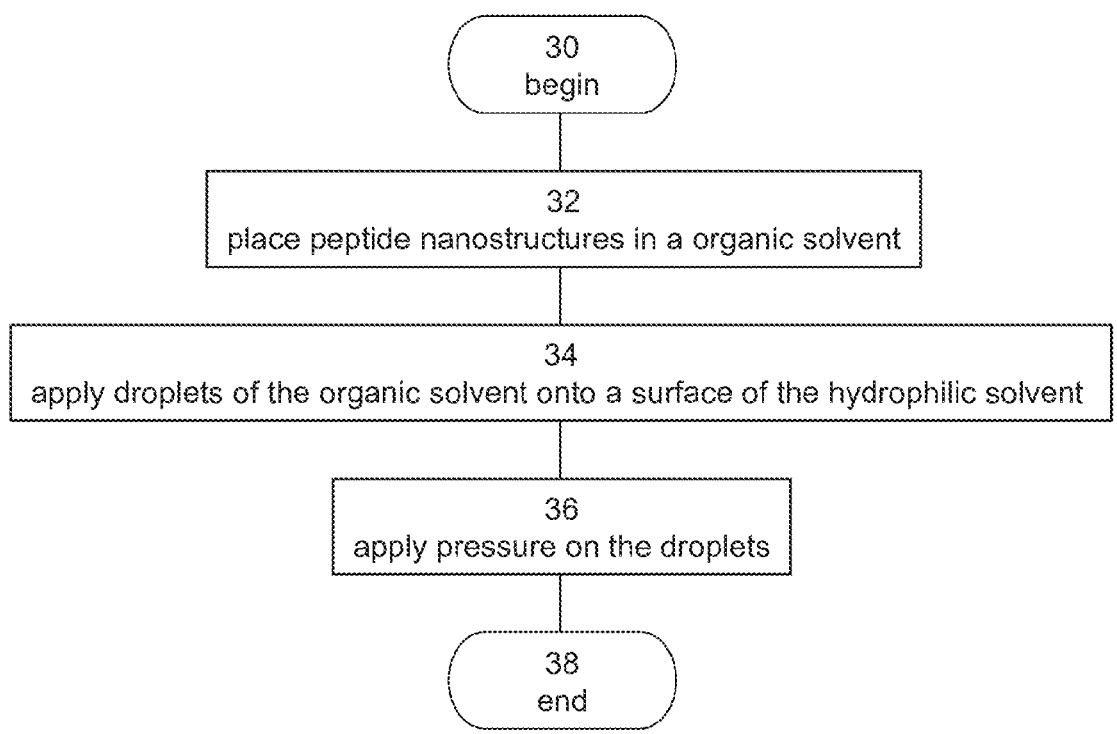
FIG. 3 is a flowchart diagram of a method suitable for forming one or more layers of peptide nanostructures, according to another preferred embodiment of the present invention.

Reference is now made to FIG. 3 which is a flowchart diagram of a method suitable for forming one or more layers of peptide nanostructures, according to another preferred embodiment of the present invention. The method begins at step 30 and continues to step 32 in which peptide nanostructures are placed in an organic solvent.

The method continues to step 34 in which one or more droplets of the organic solvent are applied onto a surface of an hydrophilic solvent. The method then continues to step 36 in which pressure is applied on the droplet of organic solvent, so as to form a layer of peptide nanostructures on the surface.

The application of pressure is preferably by moving barriers which can be made, for example, from Teflon®. The barriers reduce the surface area of the film and as a consequence the surface pressure of the layer increases. The pressure-area isotherm can be monitored continuously, e.g., by monitoring the surface are of the layer and measuring the force applied by the barrier. When pressure reaches some predetermined level, the barriers are stopped such that the layer is substantially in a steady state.

The layers can then be transferred to a substrate by any way known in the art, for example, the Langmuir-Blodgett technique or the Langmuir-Schaeffer technique.

When a Langmuir-Blodgett technique is employed, the substrate is preferably immersed a vertically through the layer. The substrate is then pulled up and the layer is transferred onto the substrate by lateral compression.

When a Langmuir-Schaeffer is employed, the substrate is descended horizontally onto the layer. Once a contact is made between the layer and the substrate, the substrate is extracted with the layer on it.

According to a preferred embodiment of the present invention the film can be subjected to a doping procedure. Doping procedures are known in the art and are found, for example, in the Handbook for conductive polymers, Edited by Terje A. Skotheim Vol. 1, 1986. This embodiment is particularly useful when it is desired to form a film with conductive properties.

Figure 4:
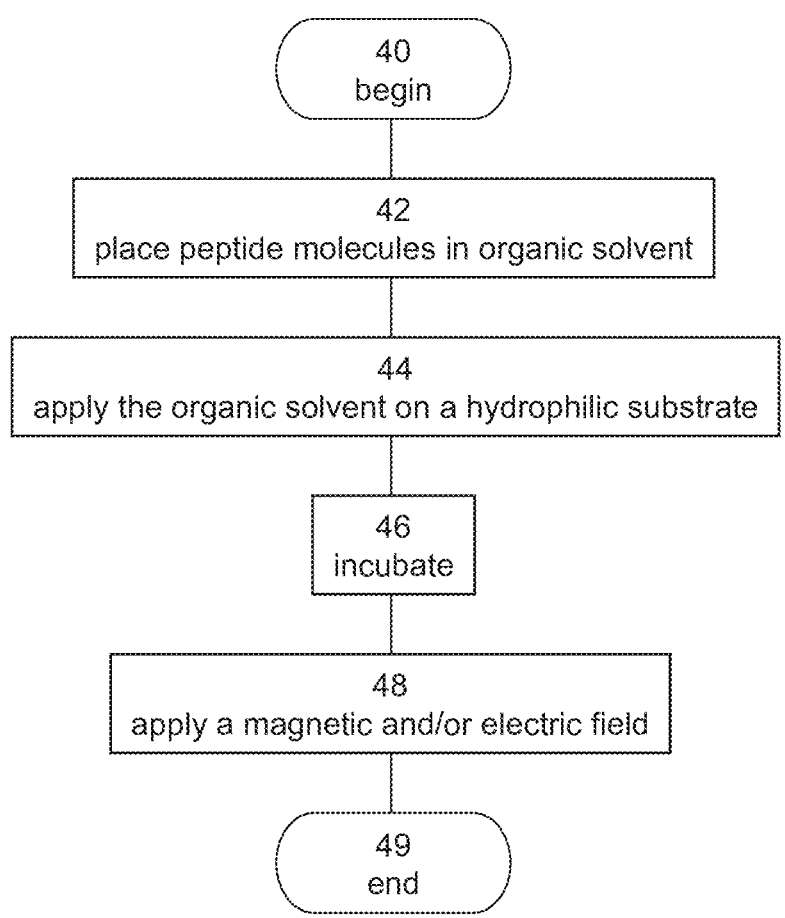
FIG. 4 is a flowchart diagram of a method suitable for forming an array or film of peptide nanostructures on a substrate, according to another preferred embodiment of the present invention.

Reference is now made to FIG. 4 which is a flowchart diagram of a method suitable for forming an array or film of peptide nanostructures on a substrate, according to a preferred embodiment of the present invention. The method begins at step 40 and continues to step 42 in which peptide molecule are placed in an organic solvent, such as, but not limited to, Hexaflorupropanol. The method continues to step 44 in which the organic solvent is applied on a substrate, such as, but not limited to, a siliconized glass an ITO glass and the like. The method then proceeds to step 46 in which the substrate is incubated under conditions which allow the peptide molecules to form an array or film of peptide nanostructures on the substrate. The incubation conditions are preferably such that the nanostructures are self-assembled as further detailed hereinabove.

When the nanostructures are responsive to a magnetic and/or electric field (i.e., when a magnetic and/or electric field exerts a force on the nanostructures), the method preferably continues to step 48 in which the substrate is subjected to a magnetic and/or electric field. The advantage of this embodiment, is that the forces can facilitate the assembling and/or alignment of the nanostructures on the substrate. Step 48 can be executed subsequently or contemporaneously with step 46.

The method ends at step 49.

Performing one or more of the above methods according to present embodiments successfully produces a thin film of peptide nanostructures. In accordance with preferred embodiments of the present invention, the thin film is at least 100 nm$^2$, more preferably at least 1 μm$^2$, more preferably at least 10 μm$^2$ in area size.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Example 1

Thin film of peptide nanostructures was manufactured, in accordance with preferred embodiments of the present invention.

Figure 5A:
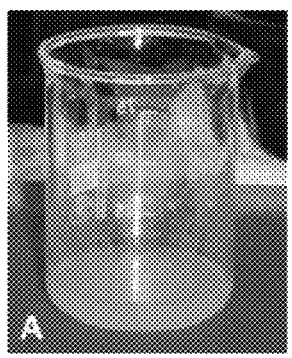
FIGS. 5A-C show a process of manufacturing a thin film in accordance with preferred embodiments of the present invention.
Figure 5B:
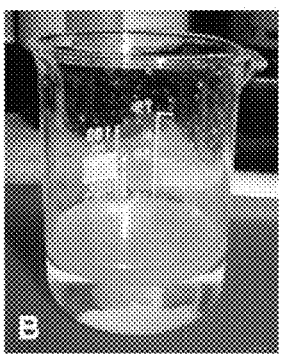
Figure 5C:
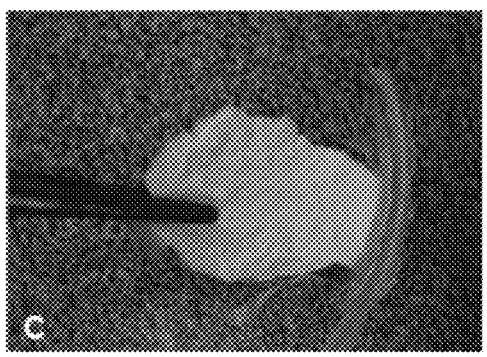

The manufacturing process is shown in FIGS. 5A-C. In a first step, shown in FIG. 5A, Boc-FF—COOH dipeptide was dissolved in benzene to a concentration of 10 mg/ml and placed in a reaction beaker. In a second step, shown in FIG. 5B, a water solution was added into the reaction beaker. As shown in FIG. 5B, an interface was formed between the benzene and the water solution. The benzene and the water solution were incubated for several hours. FIG. 5C shows a film of Boc-FF—COOH dipeptide which was formed at the interface after incubation.

Example 2

The Langmuir-Blodgett technique was employed to manufacture a thin film of peptide nanostructures, in accordance with preferred embodiments of the present invention.

A droplet of Boc-FF—COOH dipeptide was dissolved in chloroform-methanol (9:1) to a concentration of 1 mg/ml. The resulted solution was then applied on a surface of water in a Langmuir-Blodgett trough. Moving barriers, positioned at the ends of the trough were used to apply pressure on the droplet, and a film of nanostructures was formed.

Figure 6:
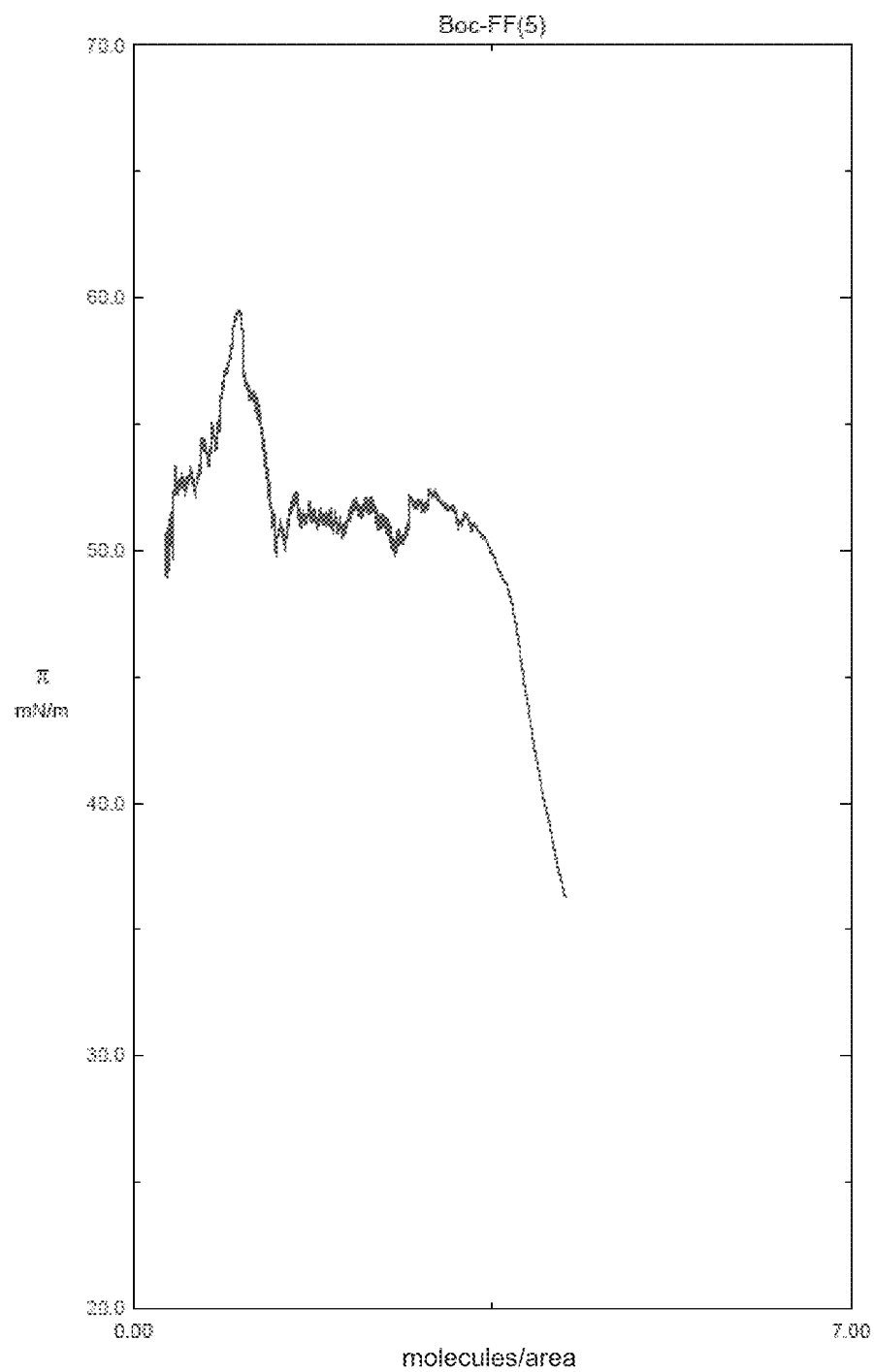
FIG. 6 is a pressure-area isotherm obtained during manufacturing of a thin film using Langmuir-Blodgett technique and in accordance with preferred embodiments of the present invention.

FIG. 6 shows a pressure-area isotherm obtained while applying the pressure. As shown in FIG. 6, the surface tension increases when the surface area is decreased, and peptide molecules are assembled together into a monolayer, which is further compressed into a film.

Example 3

An array of peptide nanostructures was manufactured on a substrate, in accordance with preferred embodiments of the present invention.

Diphenylalanine peptide was dissolved to a concentration of 100 mg/ml in 1,1,1,3,3,3-Hexafluoropropanol. 30 μl of the solution were applied onto siliconized glass and let to dry in room temperature.

Figure 7A:
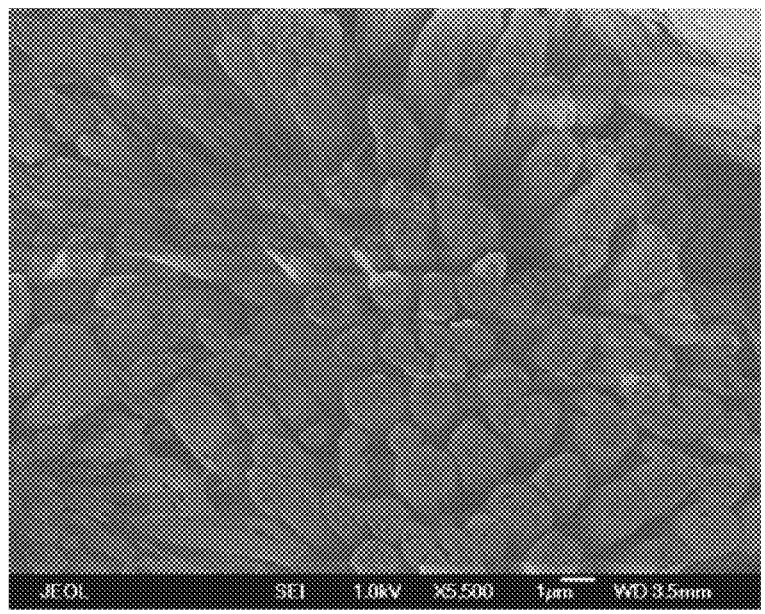
FIGS. 7A-B are high-resolution scanning electron microscope images, showing a low magnification (FIG. 7A) and a high magnification (FIG. 7B) of an aligned array of peptide nanotubes formed on a substrate, according to the teaching of various exemplary embodiments of the present invention.
Figure 7B:
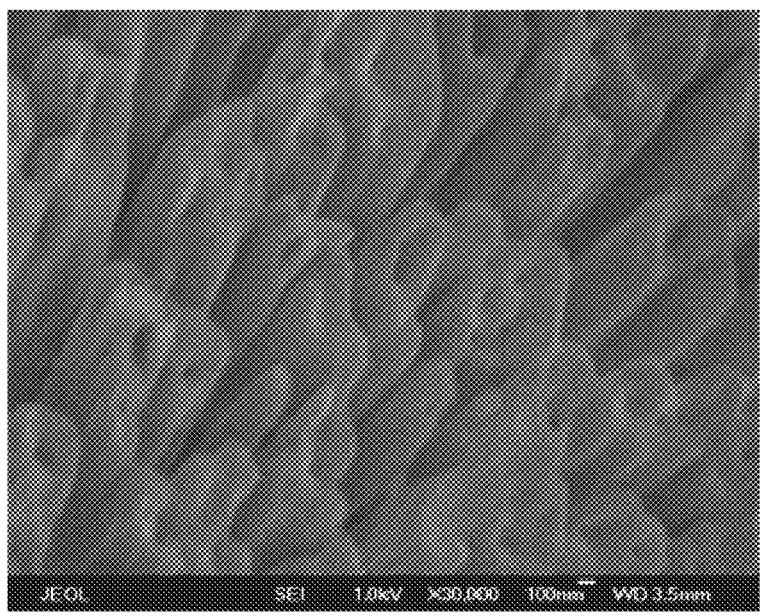

FIGS. 7A-B are a low magnification (FIG. 7A) and a high magnification (FIG. 7B) images of the substrate, obtained using a high-resolution scanning electron microscope. As shown in FIGS. 7*a-b*, an aligned array of peptide nanotubes was formed on the substrate.

Example 4

Tubular nanostructures were formed from naphthylalanine-naphthylalanine (Nal-Nal) dipeptides, in accordance with preferred embodiment of the present invention. The Chemical structure of the (Nal-Nal) dipeptide is schematically shown in FIG. 8.

Fresh stock solutions of Nal-Nal dipeptides were prepared by dissolving lyophilized form of the peptides in 1,1,1,3,3,3-hexafluoro-2-propanol (HFIP, Sigma) at a concentration of 100 mg/mL. To avoid any pre-aggregation, fresh stock solutions were prepared for each experiment.

The peptides stock solutions were diluted into a final concentration of 2 mg/mL in double distilled water, then the samples were placed on 200 mesh copper grid, covered by carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.

FIG. 9 is an electron microscope image of the samples, captured a few minutes after the dilution of the peptide stock into the aqueous solution. As shown, the dipeptides form thin (from several nanometers to a few tens of nanometers in diameter) and elongated (several microns in length) tubular structures.

Example 5

Tubular and planar nanostructures were formed from by four different dipeptides, in accordance with preferred embodiment of the present invention.

The following dipeptides were used: (Pentafluoro-Phenylalanine)-(Pentafluoro-Phenylalanine), (Iodo-Phenylalanine)-(Iodo-Phenylalanine), (4-Phenyl phenylalanine)-(4-Phenyl phenylalanine) and (P-nitro-Phenylalanine)-(P-nitro-Phenylalanine).

For the first two dipeptides [(Pentafluoro-Phenylalanine)-(Pentafluoro-Phenylalanine) and (Iodo-Phenylalanine)-

(Iodo-Phenylalanine)] fresh stock solutions were prepared by dissolving lyophilized form of the peptides in DMSO at a concentration of 100 mg/mL.

For the third and fourth dipeptides [(4-Phenyl phenylalanine)-(4-Phenyl phenylalanine) and (P-nitro-Phenylalanine)-(P-nitro-Phenylalanine)], fresh stock solutions were prepared by dissolving lyophilized form of the peptides in 1,1,1,3,3,3-hexafluoro-2-propanol (HFIP, Sigma) at a concentration of 100 mg/mL. To avoid any pre-aggregation, fresh stock solutions were prepared for each experiment.

The peptides stock solutions were diluted into a final concentration of 2 mg/mL in double distilled water.

In the case of (P-nitro-Phenylalanine)-(P-nitro-Phenylalanine) the final concentration was 5 mg/mL.

Subsequently, the samples were placed on 200 mesh copper grid, covered by carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.

FIGS. 10A-D are electron microscope images of the four samples, captured a few minutes after the dilution of the peptide stock into the aqueous solution.

Figure 10A:
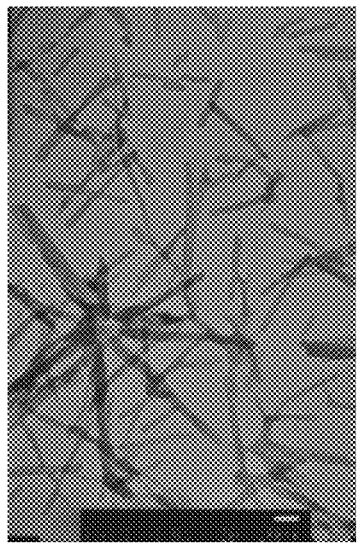
FIGS. 10A-D are electron microscope images of tubular and planar nanostructures assembled from the following aromatic-homodipeptides: (pentafluoro-phenylalanine)-(pentafluoro-phenylalanine) (FIG. 10A), (iodo-phenylalanine)-(iodo-phenylalanine) (FIG. 10B), (4-phenyl phenylalanine)-(4-phenyl phenylalanine) (FIG. 10C), and (p-nitro-phenylalanine)-(p-nitro-phenylalanine) (FIG. 10D).
Figure 10B:
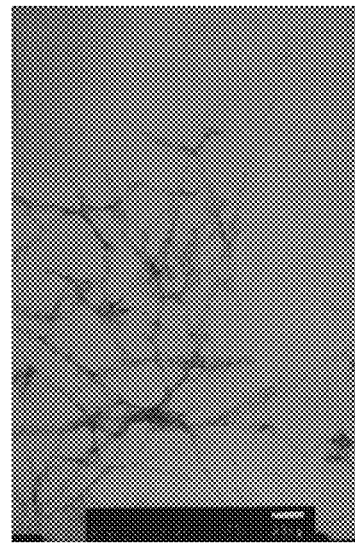
Figure 10C:
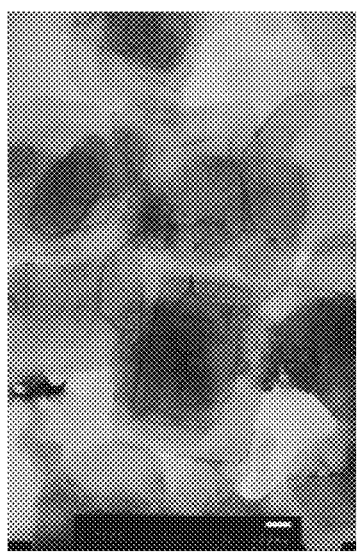
Figure 10D:
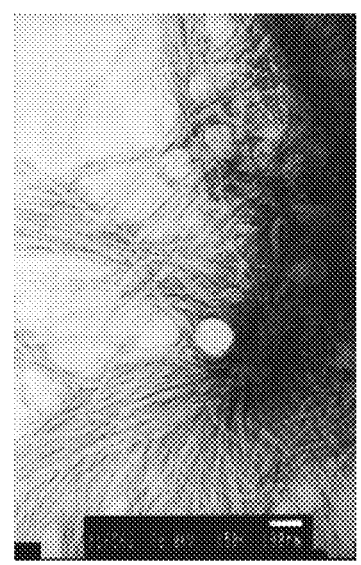

FIG. 10A shows tubular assemblies formed by the (Pentafluoro-Phenylalanine)-(Pentafluoro-Phenylalanine)dipeptide, FIG. 10B shows tubular structures assembled by (Iodo-Phenylalanine)-(Iodo-Phenylalanine), FIG. 10 C shows planar nanostructures formed by (4-Phenyl phenylalanine)-(4-Phenyl phenylalanine), and FIG. 10D shows fibrilar assemblies of (P-nitro-Phenylalanine)-(P-nitro-Phenylalanine).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A fiber comprising a plurality of peptide nanostructures, wherein each peptide in each of said plurality of peptide nanostructures comprises no more than 4 amino acids, at least one of said 4 amino acids being an aromatic amino acid, the fiber being at least 100 nm in length.

2. The fiber of claim 1, wherein at least one of said peptides comprises at least two aromatic amino acids.

3. The fiber of claim 2, wherein each peptide in each of said peptide nanostructures is a homodipeptide.

4. The fiber of claim 1, wherein said nanostructures at least partially enclose a material therein.

5. The fiber of claim 1, being producible by subjecting said peptide nanostructures, in solution, to an electric field.

6. The fiber of claim 5, being collected on a precipitation electrode.

7. The fiber of claim 6, being collected on a precipitation electrode by rotating said precipitation electrode so as to wind the fiber around said precipitation electrode.

8. The fiber of claim 6, being collected on a precipitation electrode by moving the fiber relative to said precipitation electrode so as to provide a nonwoven mat of said peptide nanostructures.

9. A nonwoven article comprising a plurality of electrospun fibers, wherein at least one of said plurality of electrospun fibers is the fiber of claim 1.

10. The fiber of claim 9, wherein at least one of said peptides comprises at least two aromatic amino acids.

11. The nonwoven article of claim 9, wherein each peptide in each of said peptide nanostructures is a homodipeptide.

* * * * *